(12) United States Patent
Jones

(10) Patent No.: US 6,315,526 B1
(45) Date of Patent: Nov. 13, 2001

(54) MOUNTING ARRANGEMENT

(75) Inventor: Richard L. Jones, Beecroft (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/489,229

(22) Filed: Jan. 21, 2000

(30) Foreign Application Priority Data

Jan. 21, 1999 (AU) .................................................. PP8269

(51) Int. Cl.[7] .......................... F04B 17/00; F04B 35/04; A61M 1/00
(52) U.S. Cl. ............... 417/363; 417/423.15; 417/423.14; 604/151
(58) Field of Search .............................. 417/363, 423.15, 417/423.14; 604/151

(56) References Cited

U.S. PATENT DOCUMENTS

| | | | |
|---|---|---|---|
| 3,731,620 | * 5/1973 | Klemmer | 101/23 |
| 4,978,281 | * 12/1990 | Conger, IV | 417/423.15 |
| 5,127,622 | * 7/1992 | Whelpley et al. | 248/550 |
| 5,564,963 | * 10/1996 | Chan | 446/179 |
| 6,216,691 | * 4/2001 | Kenyon et al. | 128/205.18 |

FOREIGN PATENT DOCUMENTS

2201222-A * 8/1988 (GB) .............................. F16F/9/00

* cited by examiner

Primary Examiner—Charles G. Freay
Assistant Examiner—Timothy P. Solak
(74) Attorney, Agent, or Firm—Pillsbury Winthrop LLP (57) ABSTRACT

The mounting arrangement (10) for a fluid displacement device (12) comprises an inflatable cushion device (16) adapted to support the fluid displacement device (12) and in fluid communication with the fluid displacement device (12). A portion of the fluid displaced by the fluid displacement device (12) inflates and/or maintains inflated the cushion device (16).

14 Claims, 8 Drawing Sheets

MOUNTING ARRANGEMENT

FIELD OF THE INVENTION

The present invention relates to a mounting arrangement and in particular a mounting arrangement for a fluid displacement device.

The invention has been developed primarily for mounting an electric motor and lower assembly within the housing of a Continuous Positive Airway Pressure (CPAP) treatment apparatus used in the CPAP treatment of, for example, Obstructive Sleep Apnea (OSA) and other ventilatory assistance treatments such as Non Invasive Positive Pressure Ventilation (NIPPV) and will be described hereinafter with reference to tis& application. However, it will be appreciated that the invention is not limited to this particular field of use and is equally suited in mounting various types of fluid displacement devices including fans, pumps and the like.

BACKGROUND OF THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 4–20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. The gas supply is connected to a conduit or tube, which in turn is connected to a patient mask which incorporates, or has in close proximity, an exhaust to atmosphere for venting exhaled gases. The blower is typically driven by an electric motor controlled by a servo-controller which is in turn under the control of a microcontroller unit.

The blower/motor assembly has hitherto been either directly mounted to the chassis or body of the CPAP apparatus, or isolated therefrom, by foam or other elastomeric sheets or moulded components to dampen vibration and minimise radiated noise. The use of foam sheets is time consuming and expensive as several sections of sheet may have to be installed. The installation of moulded foam components is less time consuming but they are more expensive to produce.

Other rotating or reciprocating machines use inflatable cushions to dampen the machine's vibration by interposing one or more of the inflatable cushions between the machine and its chassis, housing, ground or other supporting structure. There are two main types of inflatable cushions.

A first type is inflated or filled and thereafter sealed. A disadvantage of this type is they leak and collapse if punctured or otherwise damaged. As a consequence, they are not suitable for use in CPAP apparatus which are sealed during manufacture and not serviceable by customers.

A second type rely on a dedicated constant or intermittent fluid supply to maintain inflation. A disadvantage of this type is the additional complexity and costs associated with the dedicated fluid supply. This second type is also particularly unsuitable for CPAP treatment apparatus which are desirably made as small and light-weight as possible.

It is an object of the present invention to substantially overcome or at least ameliorate one or more of the deficiencies of the prior art.

SUMMARY OF THE INVENTION

Accordingly, in a first aspect, the present invention provides a mounting arrangement for a fluid displacement device, the mounting arrangement comprising an inflatable cushion device adapted to support the fluid displacement device and in fluid communication with the fluid displacement device, whereby a portion of the fluid displaced by the fluid displacement device inflates and/or maintains inflated the cushion device.

Preferably, the cushion device is in fluid communication with an outlet or interior of the fluid displacement device. The fluid displacement device is preferably a blower, turbine or fan driven by an electric motor.

In an embodiment, the mounting arrangement includes a one way valve interposed between the cushion device and the fluid displacement device, the valve being array to only allow fluid transmittal from the fluid displacement device to the cushion device.

In another embodiment, the mounting arrangement includes a pressure regulation valve interposed between the cushion device and the fluid displacement device, or between the cushion device and a zone of lower pressure thin the cushion device (such as atmosphere), the valve being arranged to limit pressurisation of the cushion device to a predetermined maximum.

In a further embodiment, the mounting arrangement includes the one-way valve and the pressure regulating valve.

The arrangement preferably also includes other mounting devices produced from foam or other elastomers. These mounting devices can, for example, act as displacement limiting devices when the cushion is not inflated or provide a resilient base for the cushion.

DETAILED DESCRIPTION OF THE PREFERRED EMBODIMENTS

Figure 1:
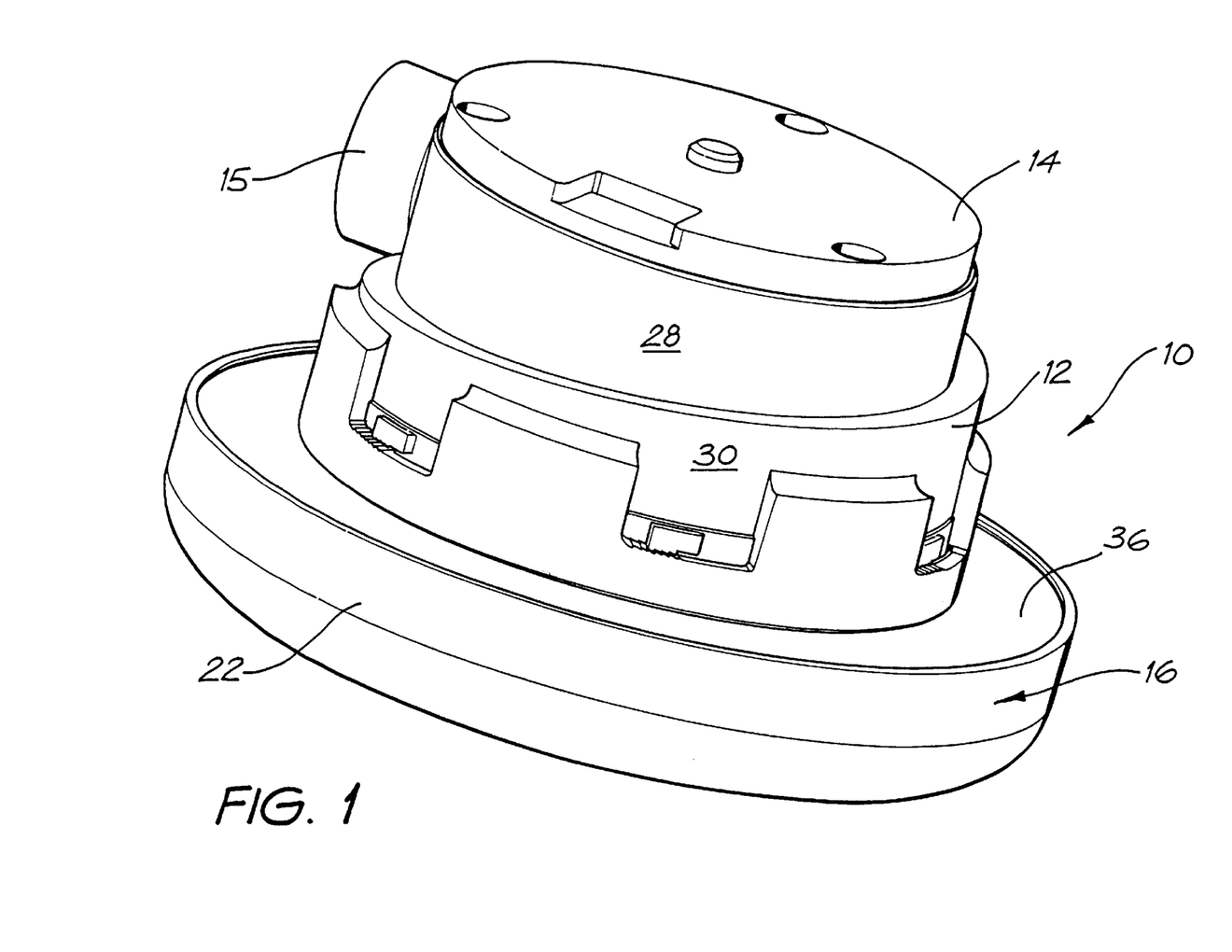
FIG. 1 is a perspective view of a first embodiment of a mounting arrangement according to the invention.
Figure 2:
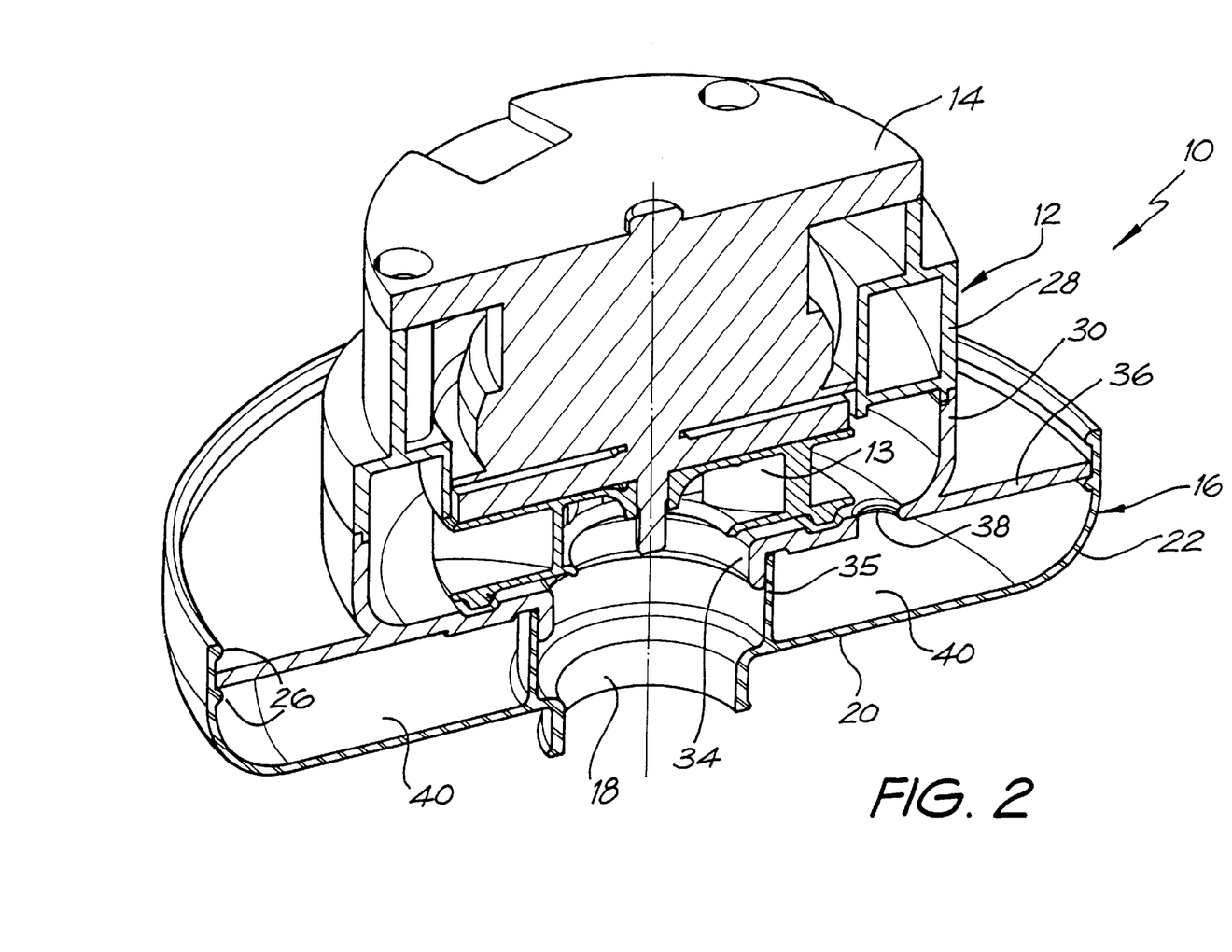
FIG. 2 is a sectional cut away view of the arrangement shown in FIG. 1.

FIGS. 1 and 2 show a first embodiment of a mounting arrangement 10 according to the present invention. The mounting arrangement 10 includes a fluid displacement device in the form of blower 12. The blower 12 has a rotor 13 rotationally driven by electric motor 14 and an outlet 15.

The underside of the blower 12 is mounted to an inflatable cushion device in the form of open-ended annular membrane 16. The membrane 16 has an internal generally cylindrical orifice 18, a generally planar annular base surface 20 and a curved side wall 22 having a pair of spaced apart internal locating rims 26 adjacent its distal edge.

The blower 12 is formed from two joined casing portions 28 and 30. The casing portion 30 contains the rotor 13 and has a central cylindrical inlet flange 34 for receiving air drawn through the orifice 18. The inlet flange 34 is a light snug fit with adjacent upper wall 35 of the orifice 18.

The casing portion 30 also includes an annular flange 36 and an opening 38. The internal diameter of the membrane sidewall 22 is slightly smaller than the external diameter of the flange 36. The membrane 16 is assembled with the flange 36 by stretching it over the flange 36 and locating the flange 36 between the two location 26. The resilience of the membrane 16 contracts it into sealing engagement with the periphery of the flange 36.

Energising the electric motor 14 causes the rotor 13 to spin. This pressurises the interior of the two housing portions 28 and 30 causing pressurised air (or other breathable gas) to be displaced from the outlet 15 (see FIG. 1). The pressurized air is also displaced through the orifice 38 into interior space 40 defined between the underside of the flange 36 and the interior of the membrane 16.

The mounting arrangement 10 is installed within a CPAP apparatus housing (not shown) with the underside of the base surface 20 supported on the chassis or some other rigid component of the housing. When the motor 14 is energised the membrane 16 is inflated which raises and supports the blower 12 and the motor 14 away from the housing chassis or the like to isolate vibration produced by the blower 12 and motor 14 from the housing.

A calculation of the lifting or supporting force generated by the membrane 16 is set out below, 1 cm $H_2O$=98.1 N/m^2

1N=101.9 g

Surface area of membrane 16 with 0.15 m outside diameter and 0.03 m inside diameter=0.0169 m^2.

Combined weight of motor 14 and blower 12=330 g

Force generated by membrane 16: 1 cm $H_2O$ will lift 98.1×0.0169=1.664N or 169.584 g Therefore 330/168.938=1.945 cm $H_2O$ will be required to lift the motor/turbine assembly.

This pressure is easily achievable by the blower/motor assembly which typically operates in the range of 2–20 cm $H_2O$ when used for treating OSA.

The main advantage of the arrangement 10 is that the membrane 16 is inflated by the blower 12. This overcomes the leakage problems of prior art devices and also obviates the need for a separate dedicated pressurised fluid source.

Another advantage is improved vibration isolation compared with other means as the only direct path for vibration is through the thin, flexible cushion (membrane) walls. The air within the cushion can also absorb vibration as the air particles are excited and dissipate the energy. As a result of the above, the inflatable cushion can be made smaller than, yet still have the same vibration isolating properties as, foam or other elastomers. This is beneficial is minimising the overall size of the CPAP apparatus.

Figure 3:
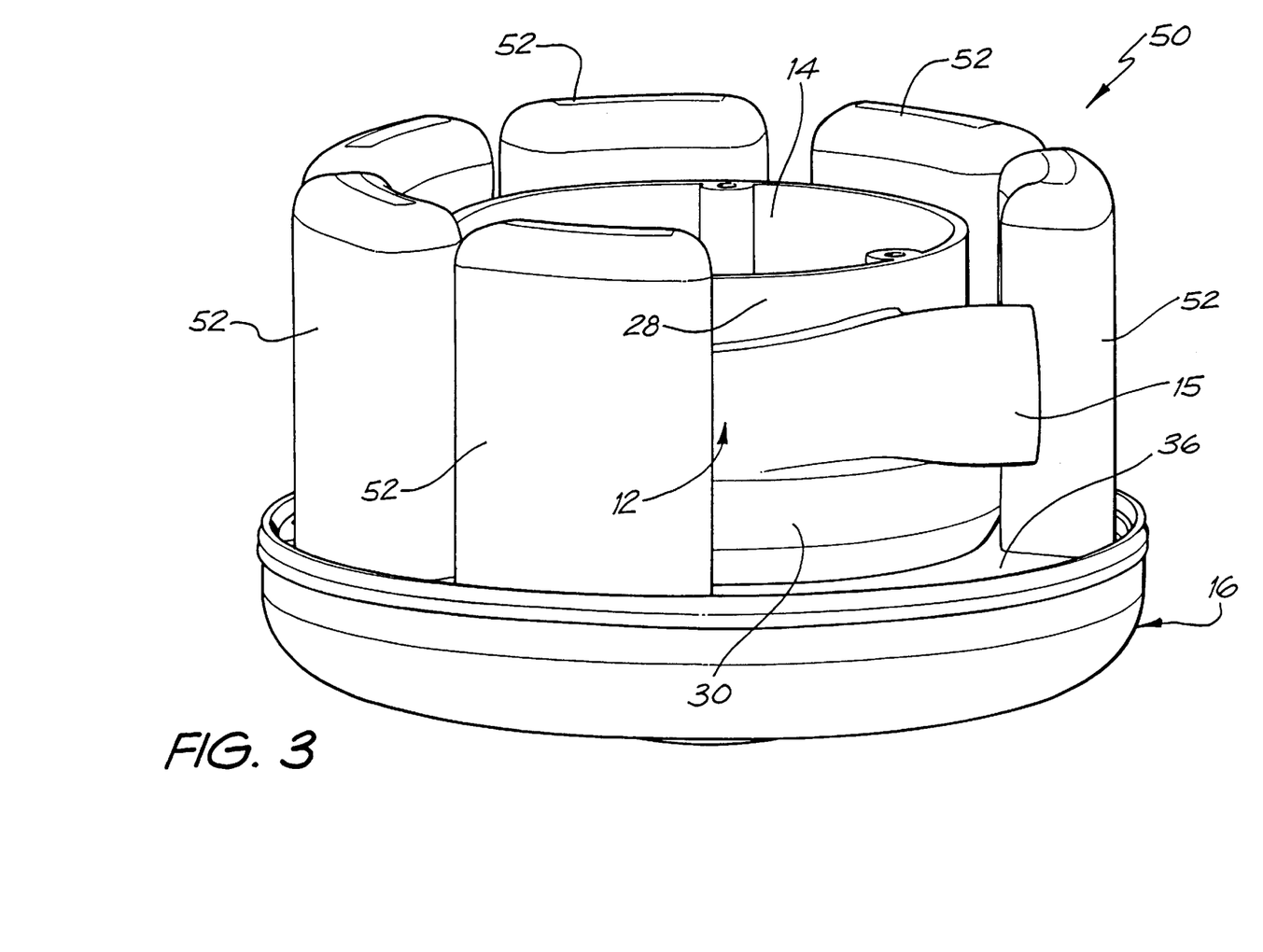
FIG. 3 is a perspective view of a second embodiment of a mounting arrangement according to the invention.

FIG. 3 shows a second embodiment of a mounting arrangement 50 according to the invention. Like reference to those used in describing the first embodiment will be used to indicate like features. The arrangement 50 is similar to the arrangement 10 except for the addition of six inflatable membranes 52 arranged around the side periphery of the blower 12 and motor 14 which further assist in mounting and locating the blower/motor assembly within the housing of the CPAP apparatus, FIGS. 4 to 15 show schematic representations of the third to fourteenth embodiments of the invention. In all of FIGS. 4 to 11 the inflatable cushion device is denoted 60, the blower/motor assembly 62. the blower inlet 64 and the blower outlet 66.

Figure 4:
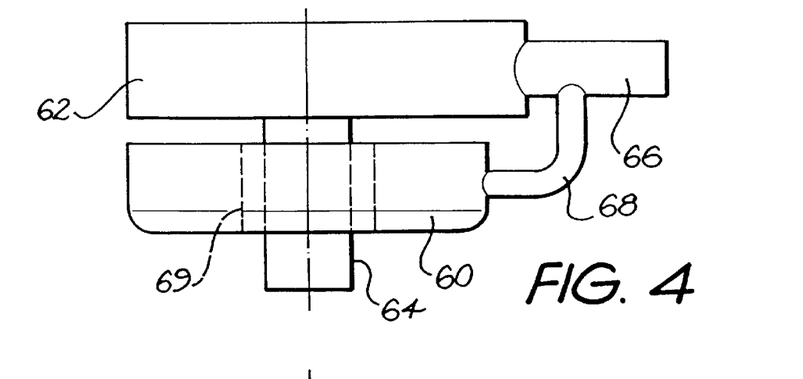
FIGS. 4 through 15 are schematic side views of third through fourteenth embodiments of mounting arrangements according to the invention.

The embodiment of FIG. 4 is similar to that shown in FIG. 1 except that it has a conduit 68 connecting the outlet 66 of the blower/motor assembly 62 to the cushion 60 rather than the opening 38. In this embodiment the inlet 64 passes through an interior opening 69 in the cushion 60 similar to the embodiment of FIG. 1.

Figure 5:
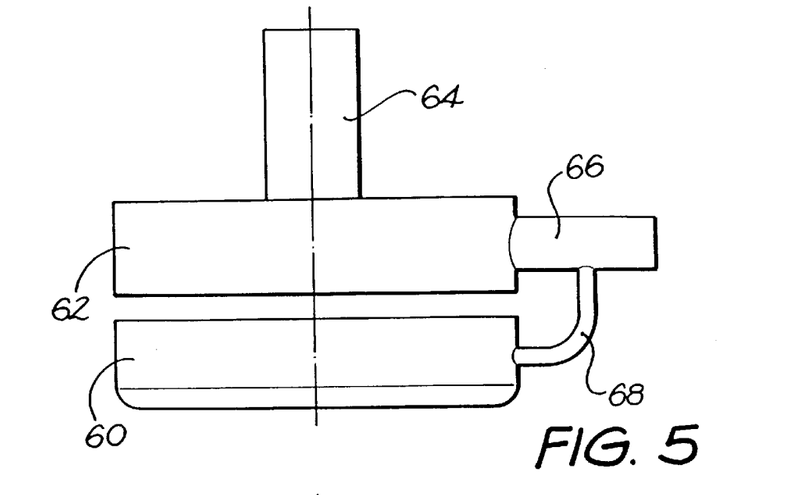

FIG. 5 is similar to the embodiment of FIG. 4 except the inlet 64 is positioned remote from the cushion 60 which thus requires no internal opening.

Figure 6:
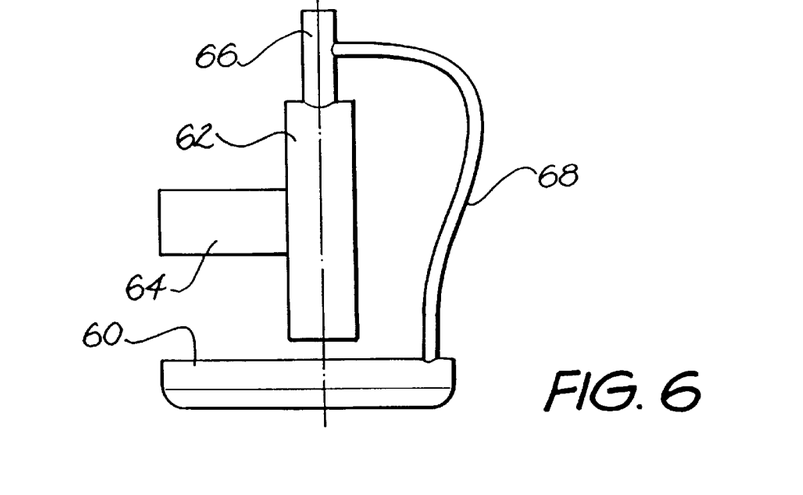

FIG. 6 shows a similar embodiment to FIG. 5 except the blower/motor assembly 62 is arranged on its side relative to the cushion 60.

Figure 7:
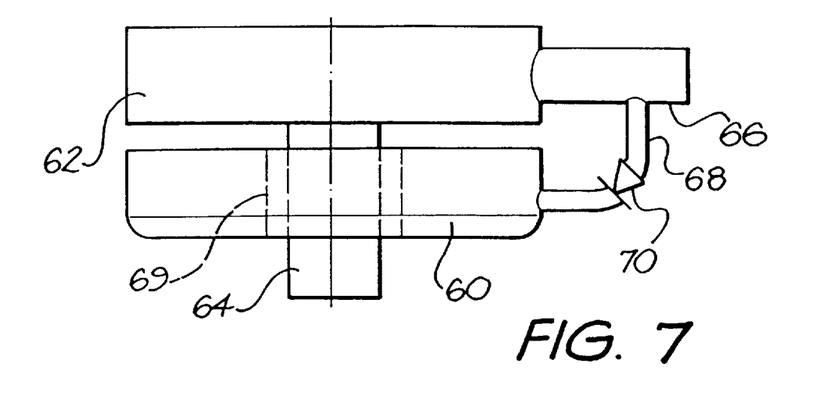

The embodiment of FIG. 7 is similar to shown in FIG. 4 but with the addition of a one-way or non-return valve 70 disposed between the outlet 66 and the cushion 60.

Figure 8:
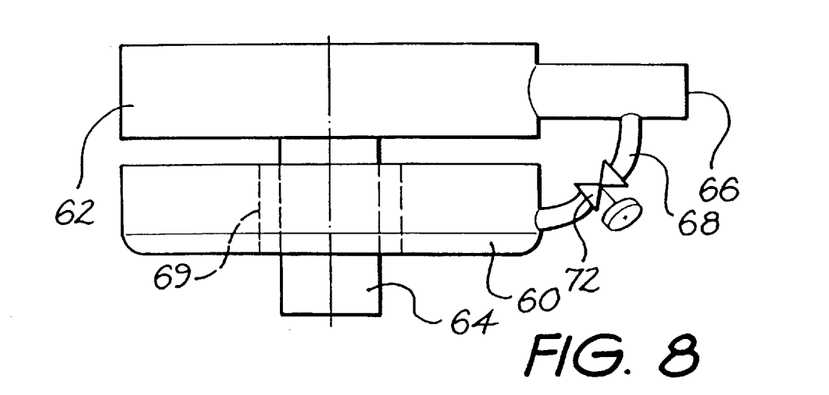

FIG. 8 is similar to the embodiment shown in FIG. 7 except the non return valve 70 is replaced by a pressure regulating valve 72.

Figure 9:
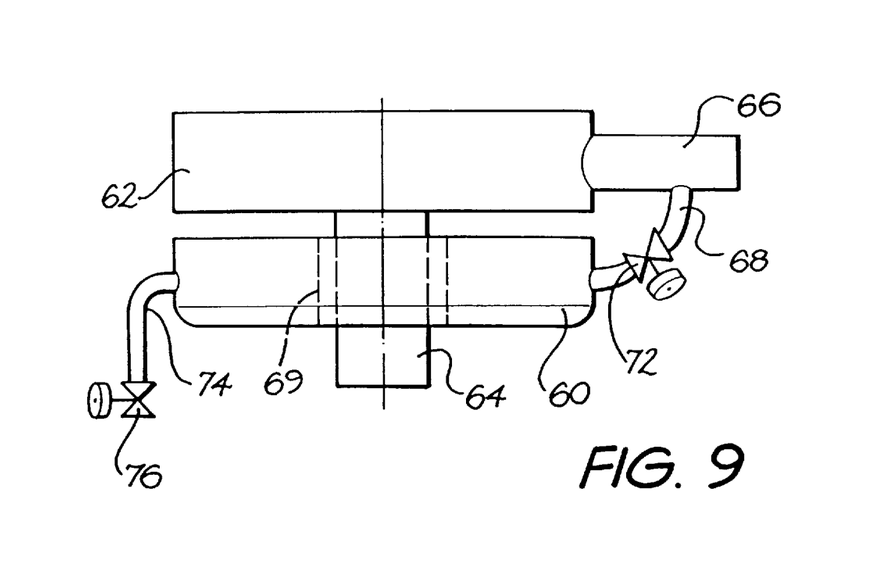

FIG. 9 is similar to the embodiment shown in FIG. 8 with the addition of a bleed conduit 74 which can vent excessive pressure to atmosphere through a pressure regulating valve 76.

Figure 10:
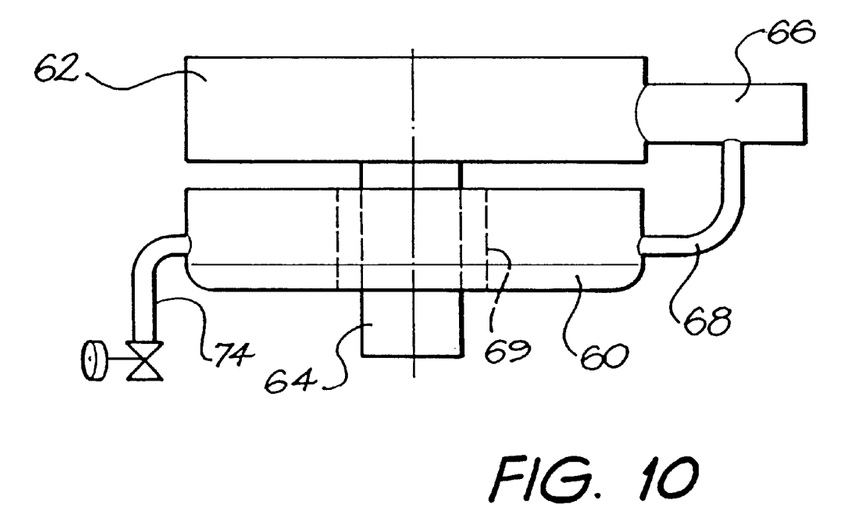

The embodiment of FIG. 10 is similar to that shown in FIG. 9 except the conduit 68 between the inlet 66 and cushion 60 does not contain a pressure regulation valve.

Figure 11:
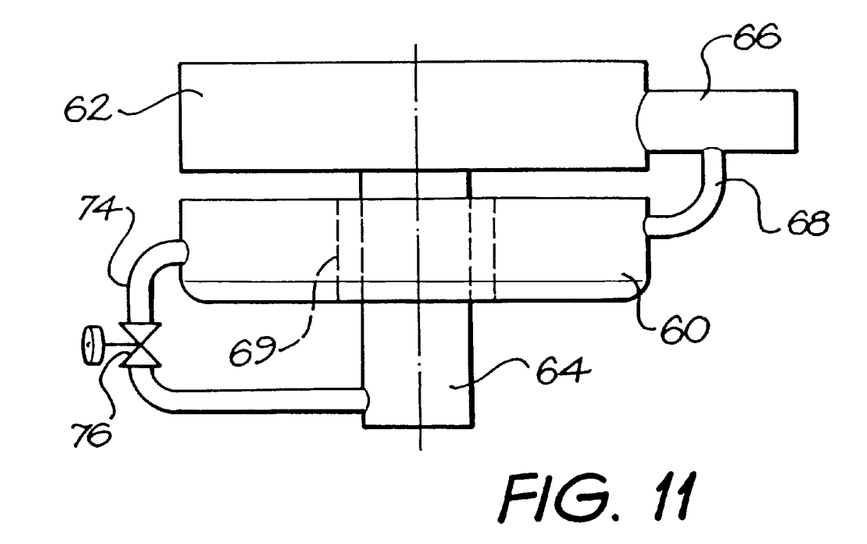

The embodiment of FIG. 11 is similar to that shown in FIG. 10 except the bleed conduit 74 and pressure regulation valve 76 vent excessive gas back to the inlet 64 of the blower/motor assembly 62.

The embodiments of FIGS. 7 to 11 have been described and are shown with the cushion device 60, inlet 64 and blower/motor assembly 62 arranged in a similar manner to that shown in FIG. 4. However, these embodiments are equally applicable to the component arrangements shown in Pigs. 5 and 6 also.

Figure 12:
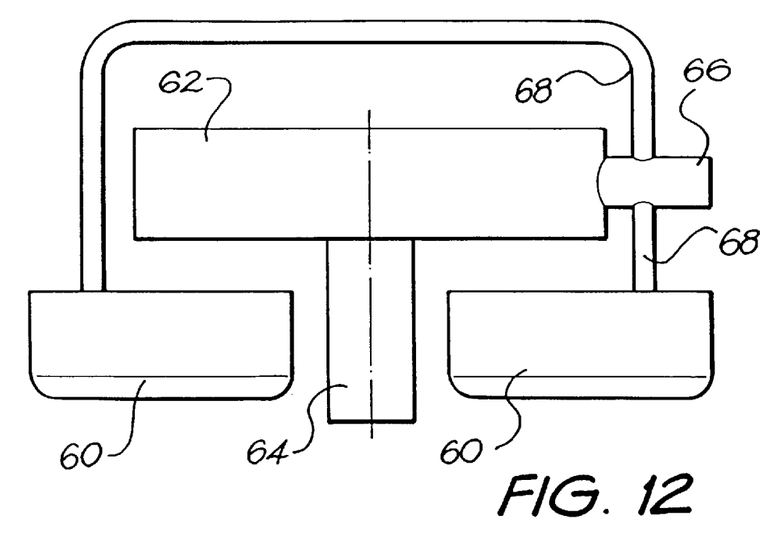

The embodiments of FIG. 12 is similar to that shown in FIG. 4 except it includes multiple (two) cushions 60 fed by multiple (two) conduits 68 arranged in parallel.

Figure 13:
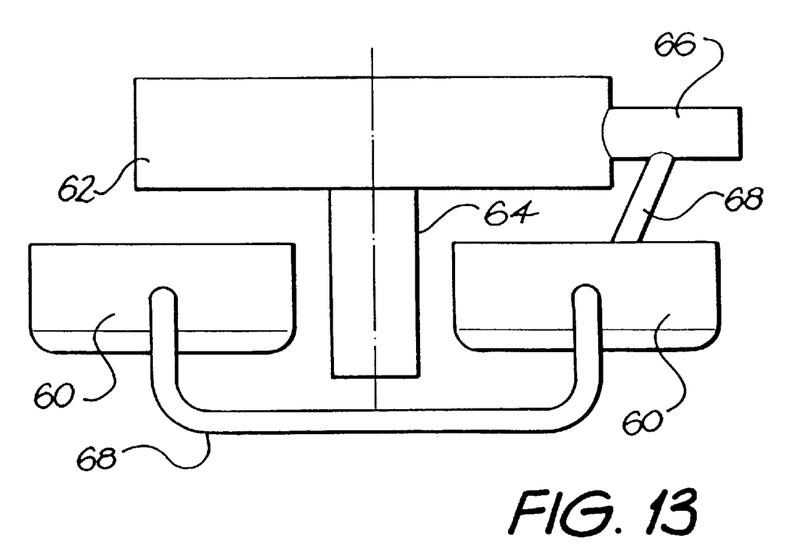

The embodiment of FIG. 13 is similar to that shown in FIG. 12 except that the multiple (two) cushions 60 are fed by multiple (two) conduits 68 arranged in series.

Figure 14:
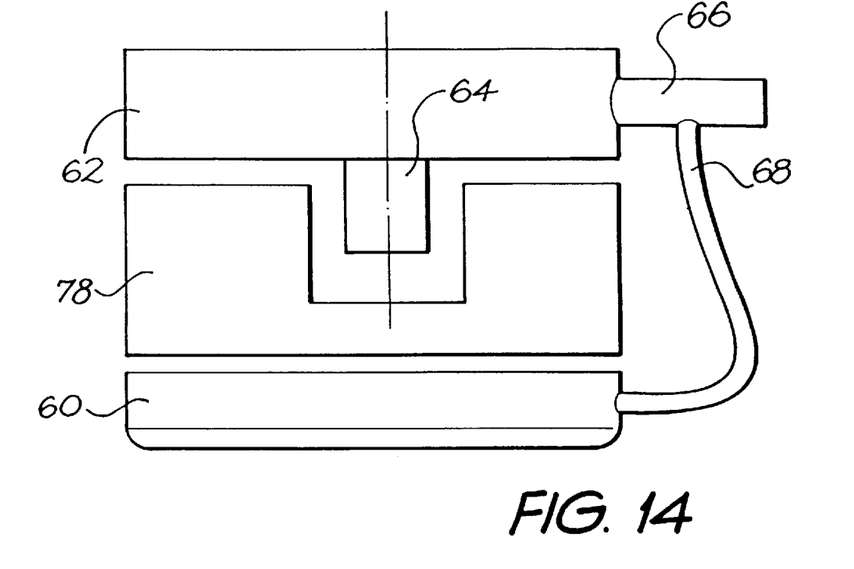

The embodiment of FIG. 14 is similar to that shown in FIG. 4 except additional components 78 are interposed between the cushion 60 and the blower/motor assembly 62.

Figure 15:
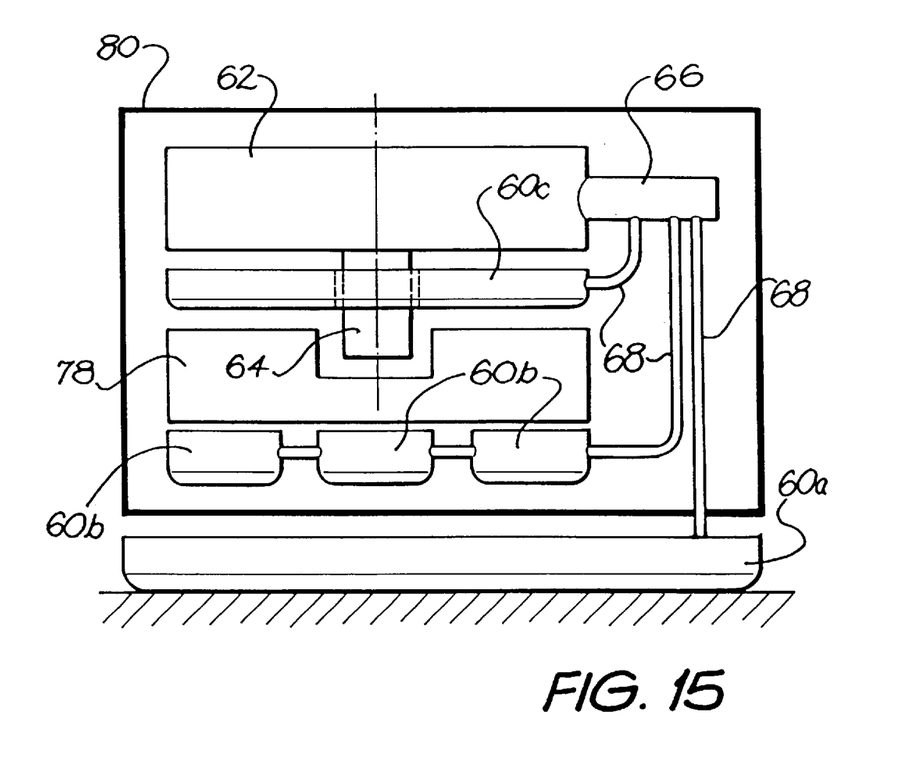

The embodiment of FIG. 15 is similar to that shown in FIGS. 14 except that an external cushion 60a supports a casing 80 around the blower/motor assembly 62. Further, inside the casing 80, there is provided a series of cushions 60*b* which support the additional components 78 and a cushion 60*c* interposed between the additional components 78 and the blower/motor assembly 62.

The embodiment shown in FIGS. 12 to 15 can also include the non-return valves or pressure regulation valves shown in FIGS. 7 to 11.

Although the invention has been described with reference to a preferred embodiment, it will be appreciated by those skilled in the art that the invention may be embodied in many other forms.

I claim:

1. A mounting arrangement for a fluid displacement device, the mounting arrangement comprising an inflatable cushion device adapted to support the fluid displacement device and in fluid communication with the fluid displacement device, whereby a portion of the fluid displaced by the fluid displacement device, at least one of inflates and maintains inflated the cushion device wherein the cushion device is an open-ended annular membrane.

2. The arrangement as claimed in claim 1, wherein the cushion device is in fluid communication with an outlet of the fluid displacement device.

3. The arrangement as claimed in claim 1, wherein the cushion device is in fluid communication with the interior of the fluid displacement device.

4. The arrangement as claimed in claim 1, wherein the fluid displacement device is a blower driven by an electric motor.

5. The arrangement as claimed in claim 1, wherein the fluid displacement device is a fan driven by an electric motor.

6. The arrangement as claimed in claim 1, further including a one way valve interposed between the cushion device and the fluid displacement device. the valve being arranged to only allow fluid transmittal from the fluid displacement device to the cushion device.

7. The arrangement as claimed in claim 1, further including a pressure regulation valve interposed between the cushion device and the fluid displacement device, the valve being arranged to limit pressurisation of the cushion device to a predetermined maximum.

8. The arrangement as claimed in claim 1, farther including a pressure regulation valve interposed between the cushion device and a zone of lower pressure than the cushion device, the valve being arranged to limit pressurisation of the cushion device to a predetermined maximum.

9. The arrangement as claimed in claim 1, further including a one way valve interposed between the cushion device and X fluid displacement device, the one way valve being arranged to only allow fluid transmittal from the fluid displacement device to the cushion device and a pressure regulation valve interposed between the cushion device and the fluid displacement device, the pressure regulation valve being arranged to limit pressurisation of the cushion device to a predetermined maximum.

10. The arrangement as claimed in claim 1, further including a one way valve interposed between the cushion device and the fluid displacement device, the one way valve being arranged to only allow fluid transmittal from the fluid displacement device to the cushion device and a pressure regulation valve interposed between the cushion device and a zone of lower pressure than the cushion device, the pressure regulation valve being arranged to limit pressurisation of the cushion device to a predetermined maximum.

11. The arrangement as claimed in claim 1, wherein tie membrane has an internal generally cylindrical orifice, a generally planar base surface and a curved side wall having a pair of spaced apart locating rim adjacent the distal edge of the side wall.

12. The arrangement as claimed in claim 1, further including additional inflatable cushion devices in fluid communication with the fluid displacement device.

13. The arrangement as claimed in claim 12, wherein all of the cushion devices are connected in fluid communication with the fluid displacement device in series.

14. The arrangement as claimed in claim 12, wherein all of the cushion devices are connected in fluid communication with the fluid displacement device in parallel.

* * * * *